United States Patent [19]

Franzmann

[11] Patent Number: 5,422,373
[45] Date of Patent: Jun. 6, 1995

[54] ANTI-ATHEROSCLEROTIC ARYL COMPOUNDS

[75] Inventor: Karl W. Franzmann, Beckenham, England

[73] Assignee: Burroughs Wellcome Co., Research Triangle Park, N.C.

[21] Appl. No.: 30,397

[22] PCT Filed: Sep. 25, 1991

[86] PCT No.: PCT/GB91/01646
§ 371 Date: Mar. 23, 1993
§ 102(e) Date: Mar. 23, 1993

[87] PCT Pub. No.: WO92/06075
PCT Pub. Date: Apr. 16, 1992

[30] Foreign Application Priority Data

Sep. 25, 1990 [GB] United Kingdom ............... 9020841

[51] Int. Cl.⁶ ............... A61K 31/17; C07C 275/30; C07C 275/10
[52] U.S. Cl. ................... 514/598; 514/467; 514/507; 514/596; 514/622; 514/824; 549/449; 560/29; 564/48; 564/52; 564/170

[58] Field of Search ............ 564/48, 52, 56; 514/596, 598, 824

[56] References Cited

U.S. PATENT DOCUMENTS

| | | | |
|---|---|---|---|
| 4,387,106 | 6/1983 | De Vries et al. | 564/49 |
| 4,397,868 | 8/1983 | De Vries | 424/322 |
| 4,623,662 | 11/1986 | De Vries | 514/596 |
| 4,857,556 | 8/1989 | Yamada et al. | 514/585 |

FOREIGN PATENT DOCUMENTS

| | | | |
|---|---|---|---|
| 0370740 | 5/1990 | European Pat. Off. | |
| 1918113 | 11/1969 | Germany | 564/52 |
| 2149394 | 6/1985 | United Kingdom . | |

Primary Examiner—Shailendra Kumar
Attorney, Agent, or Firm—Donald Brown; Lawrence A. Nielsen

[57] ABSTRACT

Diaryl urea compounds having anti-atherosclerosis activity are disclosed. Preferred compounds include the compounds 1-[4-(1,2-dimethoxyethoxy)benzyl-3-(2,4-dimethoxyphenyl)-l-heptylumea and 1-heptyl-3-(2,4-dimethoxyphenyl)-1-[4-(2-methoxyethoxymethoxy)-benzyl]urea.

4 Claims, No Drawings

ANTI-ATHEROSCLEROTIC ARYL COMPOUNDS

The present invention is concerned with a novel genus of diaryl compounds, with processes for their preparation, with medicaments containing them and with their use as therapeutic agents, particularly in the prophylaxis and treatment of atherosclerosis.

The enzyme acyl coenzyme A - cholesterol acyl transferase (ACAT) is known to be involved in the intestinal absorption of cholesterol and in the accumulation of cholesterol as cholesterol esters in the arterial wall. Thus compounds which inhibit ACAT have potent hypocholesterolaemic activity and significantly decrease arterial cholesterol deposition.

A group of clinically useful compounds known collectively as 'fibrates' give rise to a modest decrease in LDL-cholesterol, a significant decrease in triglycerides and a marked elevation of HDL-cholesterol in the plasma. The increase in the level of HDL-cholesterol is particularly important since it facilitates the removal of free cholesterol from the arterial wall for return to the liver ('reverse cholesterol transport').

It follows that a drug combining the hypocholesterolaemic/anti-atherosclerotic properties of an ACAT inhibitor with hypolipidaemic/HDL-enhancing properties would be particularly useful in the prophylaxis and treatment of atherosclerosis, the enhanced HDL-cholesterol level induced giving rise to an increase in the capacity of the reverse cholesterol transport mechanism to remove the free cholesterol resulting from ACAT inhibition in the arterial wall. Such a drug would be especially beneficial to those patients having both high serum cholesterol and triglyceride levels who are at particular risk of contracting coronary heart disease.

On the basis of the foregoing, we have discovered a series of novel compounds having potential hypolipidaemic/hypocholesterolaemic activity.

According to the present invention, therefore, there is provided a compound of formula (I)

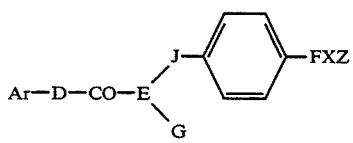

(I)

wherein

Ar is a mono- or bicyclic aromatic group optionally containing one or two heteroatoms independently selected from nitrogen, oxygen and sulphur, said group being optionally substituted by one or more atoms or groups independently selected from halogen, nitro, amino, -NRR$^1$ where R and R$^1$ are independently selected from hydrogen, $C_{1-8}$ alkyl and $C_{1-8}$ alkanoyl, cyano, carboxyalkoxy, alkoxycarbonylalkoxy, $C_{1-8}$ alkyl (including cycloalkyl and cycloalkylalkyl), $C_{1-8}$ alkoxy (including cycloalkoxy and cycloalkylalkoxy), $C_8$ thioalkyl, said alkyl, alkoxy and/or thioalkyl group(s) being optionally substituted by one or more halogen atoms, aryl, aryloxy, aralkyl and aralkyloxy, said aryl, aryloxy, aralkyl and/or aralkyloxy group(s) being optionally substituted by one or more atoms or groups independently selected from halogen, alkyl, alkoxy, alkanoyl, hydroxyalkyl, perfluoroalkyl, perfluoroalkoxy, carboxyalkoxy, alkoxycarbonylalkoxy, and $C_{3-8}$ ether or polyether groups containing from one to three oxygen atoms;

D is —$CH_2$—, —NH—, or —O—;
E is —N< or —CH<;
F is —O—or

G is $C_{3-12}$ straight, branched, or cyclic alkyl, or aralkyl, said aralkyl group being optionally substituted by one or more atoms or groups independently selected from halogen, amino, N-($C_{1-6}$ alkyl)amino, N,N-di($C_{1-6}$ alkyl)amino, $C_{1-6}$ alkyl and $C_{1-6}$ alkoxy, or a $C_{3-8}$ ether or polyether group containing one to three oxygen atoms;

J is a bond or $C_{1-6}$ straight or branched alkylene;

X is a $C_{2-8}$ straight, branched, or cyclic alkylene group optionally substituted by one or more halogen atoms or $C_{1-4}$ alkoxy groups, wherein one or two of the linear carbon atom(s) is/are replaced by oxygen; and Z is hydrogen, hydroxy, $C_{1-4}$ alkyl, $C_{2-5}$ alkanoyl, or carboxyl, said alkyl group being optionally substituted by one or more halogen atoms;

and physiologically functional derivatives thereof.

A "linear" carbon as referred to in the definition of X is a carbon located in the carbon chain or, in the case where X is an optionally substituted cyclic alkylene group, carbon chains linking the atom (oxygen or carbon according to the value of F) adjacent to the phenyl ring with Z and is not in a branch thereof.

The "physiologically functional derivatives" referred to herein are compounds which are converted in vivo to a compound of formula (I).

Preferred compounds of formula (I) having particularly good ACAT inhibiting/fibrate-like properties include those wherein Ar is phenyl or naphthyl substituted by one or more atoms or groups independently selected from halogen, $C_{1-8}$ alkyl, $C_{1-8}$ alkoxy (including cycloalkylalkoxy), said alkyl and/or alkoxy group(s) being optionally substituted by one or more halogen atoms, $C_{1-8}$thioalkyl, aryl, aryloxy and aralkoxy, said aralkoxy group being optionally substituted by alkyl, alkoyl, or hydroxyalkyl;

D is —NH—or —O—;
E is —N<;
F is —O—;

G is $C_{5-8}$ straight or branched alkyl, (4-halophenyl)$C_{1-3}$ alkyl, or [4-di($C_{1-6}$ alkyl)aminophenyl]$C_{1-3}$ alkyl;

J is $C_{1-3}$ alkylene;

X is methylene, —$CH_2CH_2$—, —$CH_2OCH_2CH_2$—, —$CH_2CH(OCH_3)$—, —$CH_2CH(OCH_2—CH_3)$—, or —$CH_2CH_2OCH_2CH_2$—; and Z is $C_{1-4}$ alkoxy;

and physiologically functional derivatives thereof.

Particularly preferred compounds of the invention are 1-[4-(1,2-dimethoxyethoxy)benzyl]-3-(2,4-dimethoxyphenyl)-1-heptylurea, 1-heptyl-3(2,4-dimethoxyphenyl)-1-[4-(2-methoxyethoxymethoxy)benzyl]urea, 1-(2, 4-difluoro-6-methoxyphenyl)-3-heptyl-3-[4-(2-methoxyethoxymethoxy)benzyl]urea, 1-(4-chloro-2-ethoxyphenyl)-3-heptyl-3-[4-(2-methoxyethoxymethoxy)benzyl]urea, 1-(4-chloro-2-trifluoromethylphenyl)-3-heptyl- 3-[4-(2-methoxyethoxymethoxy)benzyl]urea and their physiologically functional derivatives.

According to further aspects of the invention, there are also provided:

(a) compounds of formula (I) and physiologically functional derivatives thereof for use as a therapeutic agent;

(b) pharmaceutical formulations comprising a compound of formula (I) and/or one of its physiologically functional derivatives and at least one pharmaceutical carrier or excipient;

(c) the use of a compound of formula (I) or of a physiologically functional derivative thereof in the manufacture of a medicament for the prophylaxis or treatment of a clinical condition for which an ACAT inhibitor and/or a fibrate is indicated;

(d) a method for the prophylaxis or treatment of a clinical condition in a mammal, such as a human, for which an ACAT inhibitor and/or a fibrate is indicated which comprises the administration of a therapeutically effective amount of a compound of formula (I) or of a physiologically functional derivative thereof to said mammal; and (e) processes for the preparation of compounds of formula (I) and physiologically functional derivatives thereof.

With regard co aspects (a), (c) and (d), the ability of compounds of formula (I) to inhibit ACAT activity renders them useful as hypocholesteroiaemics and for reducing the steady state concentration of cholesterol and cholesterol ester in the arterial wall. Similarly, the fibrate-like activity of compounds of formula (I) renders them useful as hypolipidaemics and for increasing the capacity of the reverse cholesterol transport mechanism to remove free cholesterol from the arterial wall.

On the basis of their ability to regress established atherosclerotic plaque and retard the build-up of fresh lesions, compounds of formula (I) find application in both the prevention and treatment of atherosclerosis.

In view of their hypocholesterolaemic/hypolipidaemic properties, compounds of formula (I) and their physiologically functional derivatives may also find application in the prevention and treatment of pancreatitis, in 'shifting' the oxygen affinity of human haemoglobin to improve myocardial function, for example, in the treatment of ischaemic tissue, and as uricosuric agents for reducing elevated plasma uric acid levels arising from, for example, hypertriglyceridaemia. The compounds of the invention also exhibit calcium antagonism in the ileum, stimulate hepatic fatty acid oxidation in the liver and have the potential to lower plasma triglycerides and elevate plasma EL-cholesterol.

Hereinafter all references to "compound(s) of formula (I)" refer to compound(s) of formula (I) as defined above including their physiologically functional derivatives.

The amount of a compound of formula (I) which is required to achieve the desired biological effect will, of course, depend on a number of factors, for example, the specific compound chosen, the use for which it is intended, the mode of administration and the clinical condition of the recipient. In general, a daily dose is expected to lie in the range 10 mg to 2 g, typically 200–400 mg per day. An intravenous dose may, for example, be in the range 100 mg to 1 g, which may conveniently be administered as an infusion of from 1 mg to 100 mg per minute. Infusion fluids suitable for this purpose may contain, for example, from 0.1 mg to 10 mg, typically 1 mg, per millilitre. Unit doses may contain, for example, from 100 mg to 1 g of the active compound. Thus ampoules for injection may contain, for example, from 100 mg to 500 mg and orally administrable unit dose formulations, such as tablets or capsules, may contain, for example, from 100 mg to 1 g, typically 200 mg. In the case of physiologically acceptable salts, the weights indicated above refer to the weight of the ion derived from the salt.

For the prophylaxis or treatment of the conditions referred to above, the compounds of formula (I) may be used as the compound per se, but are preferably presented with an acceptable carrier or excipient in the form of a pharmaceutical formulation. The carrier or excipient must, of course, be acceptable in the sense of being compatible with the other ingredients of the formulation and must not be deleterious to the recipient. The carrier or excipient may be a solid or a liquid, or both, and is preferably formulated with the compound as a unit-dose formulation, for example, a tablet, which may contain from 0.05% to 95% by weight of the active compound. Other pharmacologically active substances may also be present including other compounds of formula (I). The formulations of the invention may be prepared by any of the well known techniques of pharmacy consisting essentially of admixing the components.

The formulations include those suitable for oral, rectal, topical, buccal (e.g. sub-lingual) and parenteral (e.g. subcutaneous, intramuscular, intradermal, or intravenous) administration, although the most suitable route in any given case will depend on the nature and severity of the condition being treated and on the nature of the particular compound of formula (I) which is being used.

Formulations suitable for oral administration may be presented in discrete units, such as capsules, cachets, lozenges, or tablets, each containing a predetermined amount of a compound of formula (I); as a powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association the active compound and the carrier or excipient (which may constitute one or more accessory ingredients). In general, the formulations are prepared by uniformly and intimately admixing the active compound with a liquid or finely divided solid carrier, or both, and then, if necessary, shaping the product. For example, a tablet may be prepared by compressing or moulding a powder or granules of the compound, optionally with one or more assessory ingredients. Compressed tablets may be prepared by compressing, in a suitable machine, the compound in a free-flowing form, such as a powder or granules optionally mixed with a binder, lubricant, inert diluent and/or surface active/dispersing agent(s). Moulded tablets may be made by moulding, in a suitable machine, the powdered compound moistened with an inert liquid diluent.

Formulations suitable for buccal (sub-lingual) administration include lozenges comprising a compound of formula (I) in a flavoured base, usually sucrose and atacia or tragacanth, and pastilles comprising the compound in an inert base such as gelatin and glycerin or sucrose and acacia.

Formulations of the present invention suitable for parenteral administration conveniently comprise sterile aqueous preparations of a compound of formula (I), preferably isotonic with the blood of the intended recipient. These preparations are preferably administered intravenously, although administration may also be effected by means of subcutaneous, intramuscular, or intradermal injection. Such preparations may conveniently be prepared by admixing the compound with water and rendering the resulting solution sterile and isotonic with the blood. Injectable compositions according to the invention will generally contain from 0.1 to 5% w/w of the active compound.

Formulations suitable for rectal administration are preferably presented as unit-dose suppositories. These may be prepared by admixing a compound of formula (I) with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers and excipients which may be used include vaseline, lanoline, polyethylene glycols, alcohols, and combinations of two or more thereof. The active compound is generally present at a concentration of from 0.1 to 15% w/w of the composition, for example, from 0.5 to 2%.

Compounds of formula (I) may be prepared by conventional means well known to a skilled person. Thus compounds of formula (I) wherein D is —NH— and E is —N< may be prepared by reacting a compound of formula (II)

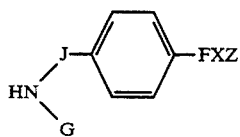 (II)

wherein F, G, J, X and Z are as hereinbefore defined, with a compound of formula (III)

 Ar—NCO (III)

wherein Ar is as hereinbefore defined, typically in an aprotic polar solvent, such as acetonitrile, optionally in the presence of a catalytic amount of base, for example, 4-dimethylaminopyridine.

Compounds of formula (II) may be prepared by reducing a compound of formula (IV)

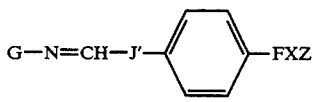 (IV)

wherein F, G, X and Z are as hereinbefore defined and J' is as hereinbefore defined for J less a terminal methylene group (or is a bond when J is methylene), typically using a hydride reducing agent, such as sodium borohydride, in a polar solvent, for example, SVM.

Compounds of formula (IV) may be prepared by reacting a compound of formula (V)

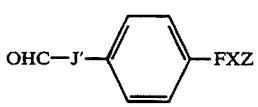 (V)

wherein F, J', X and Z are as hereinbefore defined, with a compound of formula (VI)

 G—NH₂ (VI)

wherein G is as hereinbefore defined, typically by refluxing in toluene in a Dean-Stark apparatus.

Compounds of formula (V) wherein F is —O— may be prepared by reacting a compound of formula (VII)

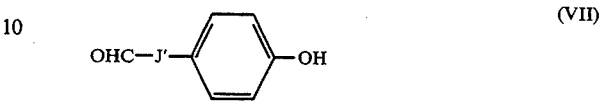 (VII)

wherein J' is as hereinbefore defined, with a compound of formula (VIII)

L—XZ (VIII) 

wherein X and Z are as hereinbefore defined and L is a suitable leaving group, for example, chloro or bromo, typically in an aprotic polar solvent, such as DCM or DMF, in the presence of a base, for example, a Tertiary amine, such as diisopropylethylamine, or sodium hydride.

Compounds of formula (II) may also be prepared by reducing a compound of formula (IV)

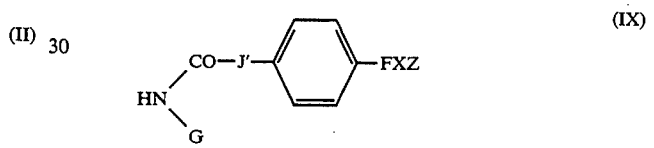 (IX)

wherein F, G, J', X and Z are as hereinbefore defined, typically using a hydride reducing agent, such as LAH, in a non-polar solvent, for example, THF, at low temperature.

Amides of formula (IX) may be prepared by reacting the corresponding carboxylic acid with a compound of formula (VI), typically in an aprotic polar solvent, such as DMF, in the presence of an amide coupling agent, for example, 1-(3-dimethylaminopropyl)-3-ethylcarbodiimide hydrochloride, a catalyst, for example, 1-hydroxybenzotriazole, and pyridine, at low temperature.

The appropriate carboxylic acid may be prepared by base hydrolysis of a corresponding ester, such as the ethyl ester, using, for example, KOH in a suitable alcohol, such as ethanol, followed by acidification.

The appropriate ester wherein F is —O— may be prepared by reacting the corresponding 4-hydroxy compound with a compound of formula (VIII) as hereinbefore defined, typically in an aprotic polar solvent, such as DMF, in the presence of a base, for example, sodium hydride and/or K₂CO₃.

The appropriate 4-hydroxy ester may be prepared by the esterification of 4-hydroxybenzoic acid using, for example, the appropriate acidified alcohol, such as ethanolic HCl or ethanol acidified with c.H₂SO₄.

Compounds of formula (III), (VI), (VII) and (VIII) are commercially available or may be prepared by methods well known to a skilled person or obtainable from the chemical literature.

Optional conversion of a compound of formula (I) to a physiologically functional derivative may be carried out by methods well known no a skilled person or obtainable from the chemical literature.

For a better understanding of the invention, the following Examples are given by way of illustration.

SYNTHETIC EXAMPLES

Synthetic Example 1

Preparation of
1-[4-(1,2-dimethoxyethoxy)benzyl]-3-(2,4-dimethoxyphenyl)-1-heptylurea (a) 4- (1.2- Dimethoxyethoxy)benzaldehyde 4-Hydroxybenzaldehyde (Aldrich, 24.4 g) was added in portions to a stirred suspension of NaH (5.3 g) in DMF (250 ml) at a temperature non exceeding 45° C. When addition was complete, the mixture was stirred until hydrogen evolution ceased and bromoacetaldehyde dimethyl actual (Aldrich, 36.6 g) was added. When addition was complete, the mixture was stirred at 85° C. for 12 hours during which time $K_2CO_3$ (1.0 g) was added after about 5 hours. The mixture was then poured into ice-water (600ml) and extracted with $EtOAc/Et_2O$ (1:1). The combined extracts were washed with 2M aqu. NaOH saturated with NaCl, treated with Hyflo/-charcoal, dried and filtered. The filtrate was evaporated in vacuo to give the desired product as a pale tan oil (34.3 g).

(b) N-n-Heptyl-4-(1,2-dimethoxyethoxy)benzylimine

A solution of the product from step (a) (10.5 g) and n-heptylamine (Aldrich, 5.8 g) in toluene (60 ml) was refluxed for 6.5 hours using a Dean-Stark apparatus. The resulting mixture was evaporated in vacuo to give the desired product as a pale tan oil (15.5 g).

(c) N-n-Heptyl-4-(1,2-dimethoxyethoxy)benzylamine

A solution of the product from step (b) (15.4 g) in SVM (20 ml) was added dropwise to a stirred suspension of $NaBH_4$ (4.0 g) in SVM (200 ml) at 0° C. over 30 minutes. When addition was complete, the mixture was allowed to warm to room temperature, stirred for 14 hours and then evaporated in vacuo. The residue was treated with water and the precipitated oil extracted with ether. The combined extracts were dried and filtered and the filtrate evaporated in vacuo to give the desired product as a pale tan oil (15.7 g).

(d) 1-[4-(1,2-Dimethoxyethoxy)benzyl]-3-(2,4-dimethoxyphenyl)-1-heptylurea 2,4-Dimethoxyphenyl isocyanate (Aldrich, 5.6 g) was added in one portion to a stirred solution of the product from step (c) (10.3 g) in acetonitrile (50 ml). The mixture was stood at room temperature for 2 days and then evaporated in vacuo to give a mobile pale tan oil which was flash chromatographed through a silica column using cyclohexane/ethyl acetate (1:1) as eluant to give the desired product as a colourless oil (13.0 g).

Elemental analysis: C 66.42 (66.39), H 8.38 (8.19), N 5.60 (5.73) 200MHz $^1$H NMR ($CDCl_3$, δ): 0.9 (m, 3H, —$CH_3$), 1.3 (m, 8H, —$(CH_2)_4$—), 1.7 (m, 2H, —$CH_2$—), 3.3 (t, 2H, —$CH_2$—), 3.5 (s, 6H, —$CH(OCH_3)_2$), 3.7 (s, 3H, —$OCH_3$), 3.8 (s, 3H, —$OCH_3$), 4.0 (d, 2H, —$CH_2$—), 4.5 (s, 2H, —$CH_2$—), 4.7 (t, 1H, —CH<), 6.4–8.0 (m, 7H, aromatics) and 6.8 (s, 1H, —NH—)

Synthetic Examples 2–78

The following compounds of formula (I) were prepared in a manner analogous to the method of Synthetic Example 1. All compounds have 200MHz $^1$H NMRs and elemental analyses consistent with the proposed structures.

2) 1-Heptyl-3-(2,4-dimethoxyphenyl)-1-[4-(2-methoxyethoxymethoxy)benzyl urea, colourless oil;

3) 1-(2,4-Difluoro-6-methoxyphenyl)-3-heptyl-3-[4-(2-methoxyethoxy methoxy)benzyl]urea, pale yellow oil;

4) 1-(2,4-Dimethoxyphenyl)-3-heptyl-3-(4-[2-(2-methoxyethoxy) ethoxy]benzyl)urea, colourless oil;

5) 1-Heptyl-1-[4-(2-methoxyethoxymethoxy)benzyl-3-(2-methoxyphenyl) urea, colourless oil;

6) 1-(2-Ethoxyphenyl)-3-heptyl-3-[4-(2-methoxyethoxymethoxy)benzyl]urea, colourless oil;

7) 1-(2,4-Dimethoxyphenyl)-3-heptyl-3-[4-(2-methoxyethoxy)benzyl] urea, colourless oil;

8) 1-(4-Chloro-2-trifluoromethylphenyl)-3-heptyl-3-[4-(2-methoxy ethoxymethoxy)benzyl]urea, colourless oil;

9) 1-(2-Ethoxyphenyl)-3-heptyl-3-[4-{2-[(2-methoxy)ethoxy)benzyl] urea, colourless oil;

10) 1-(2,4-Difluorophenyl)-3-heptyl-3-[(2-methoxyethoxy)methoxy benzyl]urea, colourless oil;

11) 1-(2,6-Difluorophenyl)-3-heptyl-3-[4-(2-methoxyethoxymethoxy) benzyl]urea, colourless oil;

12) 1-heptyl-l-[4-(2-methoxyethoxymethoxy)benzyl]-3-(2-trifluoro methoxyphenyl)urea, colourless oil;

13) 1-heptyl-l-[4-(2-methoxyethoxymethoxy)benzyl]-3-(2-methylthio phenyl)urea, nearly colourless oil;

14) 1-(4-Chloro-2-ethoxyphenyl)-3-heptyl-3-[4-(2-methoxyethoxy methoxy)benzyl]urea, colourless oil;

15) 2-Ethoxyphenyl-N-heptyl-N-[4-(2-methoxyethoxymethoxy)benzyl] carbamate, colourless oil;

16) 1-{1-Fluoro-6-[4-(1-hydroxy-2,2-dimethylpropyl)benzyloxy]phenyl)-3-heptyl-3-[4-(2-methoxyethoxymethoxy)benzyl]urea, colourless oil;

17) 1-Heptyl-1-[4-(2-methoxyethoxymethoxy)benzyl]-3-(2-methoxy-4methylthiophenyl)urea, colourless oil;

18) 1-(2-Ethoxy-4,6-difluorophenyl)-3-heptyl-3-[4-(2-methoxyethoxymethoxy)benzyl]urea, no mp (pale yellow wax);

19) 1-Heptyl-l-[4-(2-methoxyethoxymethoxy)benzyl]-3-(1-methoxy-2-naphthyl)urea, mp 46°–48° C.;

20) 1-[2-Fluoro-6-(4-pivaloylbenzyloxy)phenyl]-3-heptyl-3-[4-(2-methoxyethoxymethoxy)benzyl]urea, colourless oil;

21) 1-[2,4-Dimethoxy-6-(4-neopentylbenzyloxy)phenyl]-3-heptyl-3-[4(2-methoxyethoxymethoxy)benzyl]urea, colourless oil;

22) 1-(2,6-Difluorophenyl)-3-heptyl-3-{4-[2-(2-methoxyethoxy)ethoxy]benzyl}urea, colourless oil;

23) 1-(2,4-Dimethoxyphenyl)-3-(1,1-dimethylhexyl)-3-{4-[2-(2-methoxyethoxy)ethoxy]benzyl)urea, colourless oil;

24) 1-(4-Chlorophenyl)-3-heptyl-3-[4-(2-methoxyethoxymethoxy)benzyl]urea, mp 35°–37° C.;

25) 1-(4-Bromo-2,6-dimethylphenyl)-3-heptyl-3-[4-(2-methoxyethoxymethoxy)benzyl]urea, mp 62°–64° C.;

26) 1-(2,5-Di-t-butylphenyl)-3-heptyl-3-[4-(2-methoxyethoxymethoxy)bentyl]urea, mp 78°–80° C.;

27) N-Heptyl-N-(4-(2-methoxyethoxymethoxy)benzyl]-2,4-dimethoxyphenyl acetamide, pale tan oil;

28) 1-(2,6-Dimethoxyphenyl)-3-heptyl-3-[4-(2-methoxyethoxymethoxy)benzyl]urea, colourless oil;

29) 1-Heptyl-l-[4-(2-methoxyethoxymethoxy)benzyl-3-(2,4,6-trimethoxyphenyl)urea, colourless oil;

30) 1-(2,4-Difluoro-6-methoxyphenyl)-3-(3,3-dimethylbutyl)-3-[4-(2methoxyethoxymethoxy)benzyl]urea, very pale yellow oil;

31) 1-(2,4-Difluoro-6-methoxyphenyl)-3-(1,1-dimethyloctyl)-3-[4-methoxyethoxymethoxy)benzyl]urea, colourless oil;

32) 1-(2,4-Dimethoxyphenyl)-3-(1,1-dimethylhexyl)-3-[4-(2-methoxyethoxymethoxy)benzyl]urea, colourless oil;

33) 1-(2,4-Diethoxyphenyl)-3-heptyl-3-[4-(2-methoxyethoxymethoxy)benzyl]urea, very pale yellow oil;

34) 1-[2-Fluoro-6-(2,2,2-trifluoroethoxy)phenyl]-3-heptyl-3-[4-(2methoxyethoxymethoxy)benzl]urea, pale tan oil;

35) 1-(2,4-Dichloro-6-ethoxyphenyl)-3-heptyl-3-[4-(2-methoxyethoxymethoxy)benzyl]urea, colourless oil;

36) 1-(4-Chloro-2-ethoxyphenyl)-3-(3,3-dimethylbutyl)-3-[4-(2-methoxyethoxymethoxy)benzyl]urea, colourless oil;

37) 1-(4-Chloro-2-ethoxyphenyl)-3-[4-(2-methoxyethoxymethoxy)benzyl]3 (1-methyloctyl)urea, mp 50°-51° C.

38) 1-Heptyl-l-[4-(2-methoxyethoxymethoxy)benzyl]-3-(2-propoxyphenyl)urea, very pale yellow oil;

39) 1-Heptyl-l-[4-(2-methoxyethoxymethoxy)benzyl]-3-(2-phenoxyphenyl)urea, pale tan oil;

40) 1-(2-Ethoxynaphth-1-yl)-3-heptyl-3-[4-(2-methoxyethoxymethoxy)benzyl]urea, colourless oil;

41) 1-(2-Cyclohexylmethoxy-4-methoxy)phenyl-3-heptyl-3-[4-(2-methoxyethoxymethoxy)benzyl]urea, almost colourless oil;

42) 1-(3-Chlorothien-2-yl)-3-heptyl-3-[4-(2-methoxyethoxymethoxy)benzyl]urea, tan oil;

43) 1-(2-(4-t-butylbenzyloxy)phenyl]-3-heptyl-3-[4-(2-methoxyenhoxymethoxyl)benzyl]urea, colourless oil;

44) 1-[2-(4-t-butylbenzyloxy)-4-chlorophenyl]-3-heptyl-3-[4-(2-methoxyethoxymethoxy)benzyl]urea, colourless oil;

45) 1-[2,6-Difluoro-6-(4-neopentylbenzyloxy)-phenyl]-3-heptyl-3-(2methoxyethoxymethoxy)urea, colourless oil;

46) 1-(2,4-Difluorophenyl)-3-heptyl-3-[4-(2-methoxyethoxy)benzyl]urea, colourless oil;

47) 1-(4-Chloro-2-ethoxyphenyl)-3-heptyl-3-[4-(2-methoxyethoxy)benzyl]urea, colourless oil;

48) 1-(4-Chlorophenyl)-3-(4-ethoxymethoxybenzyl)-3-heptylurea, colourless oil;

49) 1-(2,4-Difluorophenyl)-3-(4-ethoxymethoxybenzyl)-3-heptylurea, colourless oil;

50) 1-(2,5-Di-t-butylphenyl)-3-(4-ethoxymethoxybenzyl)-3-heptylurea, mp 98°-100° C.;

51) 1-(4-Ethoxymethoxy)benzyl-3-(2,6-difluorophenyl)-1-heptylurea, no mp (colourless waxy needles);

52) 1-(2,4-Difluorophenyl)-3-heptyl-3-(4-methoxymethoxybenzyl)urea, colourless oil;

53) 1-(2,4-Dimethoxyphenyl)-3-heptyl-3-(4-methoxymethoxybenzyl)urea, colourless oil;

54) 1-(2-Ethoxyphenyl)-3-heptyl-3-(4-methoxymethoxybenzyl)urea, colourless oil;

55) 1-(2-Ethoxyphenyl)-3-heptyl-3-(2,2-dimethoxyethoxybenzyl)urea, colourless oil;

56) 1-(2,4-Difluorophenyl)-3-heptyl-3-(2,2-dimethoxyethoxybenzyl)urea, colourless oil;

57) 1-[4-(2,2-Diethoxyethoxy)benzyl]-3-(2,4-dimethoxyphenyl)-l-heptylurea, colourless oil;

58) 1-[4-(2,2-Diethoxyethoxy)benzyl]-3-(2-ethoxyphenyl)-l-heptylurea, colourless oil;

59) 1-(2-Ethoxyphenyl)-3-heptyl-3-{2-[4-(2-methoxyethoxymethoxy)phenyl] ethyl]urea, colourless oil;

60) 1-(2,4-Dimethoxyphenyl)-3-heptyl-3-{2-[4-(2-methoxyethoxymethoxy)phenyl]ethyl}urea, pale tan oil;

61) 1-(2,4-Difluorophenyl)-3-heptyl-3-{2-[4-(2-methoxyethoxymethoxy)phenyl]ethyl]urea, colourless oil;

62) 1-(2,6-Diisopropylphenyl)-3-{4-[2-(1,3-dioxalan-2-yl)ethoxy]benzyl)-3-heptylurea, mp 130°-132° C.;

63) 1-{4-[2-(1,3-Dioxalan-2-yl)ethoxy]benzyl}-3-(2-ethoxyphenyl)-1-heptylurea, colourless oil;

64) 1-(2,4-Dimethoxyphenyl)-3-{4-[2-(1,3.-dioxalan-2-yl)ethoxy]benzyl}-3-heptylurea, colourless oil;

65) 1-(2,4-Dimethoxyphenyl)-3-[4-(1,3-dioxolan-2-ylmethoxy)benzyl]-3-heptylurea, colourless oil;

66) 1-(2,4-Difluorophenyl)-3-[4-(1,3-dioxolan-2-ylmethoxy)benzyl]-3-heptylurea, colourless oil;

67) 1-(2-Ethoxyphenyl)-3-[4-(1,3-dioxolan-2-ylmethoxybenzyl)-3-heptylurea, colourless oil;

68) 2-Methoxyethyl-4-[3-(2-ethoxyphenyl)-1-heptylureidomethyl]benzoate, colourless oil;

69) 2-Methoxyethyl-4-[3-(2,4-difluorophenyl)-1-heptylureidomethyl]benzoate, colourless oil;

70) 2-Methoxyethyl-4-[3-(2,4-dimethoxyphenyl)-1-heptylureidomethyl]benzoate, very pale yellow oil;

71) 4-{4-[3-(2-Ethoxyphenyl)-1-heptylureidomethyl]-phenoxy}butanl-ol, colourless oil;

72) 4-{4-[3-(2,4-Dimethoxyphenyl)-1-heptylureidomethyl]phenoxy}butanl-ol, pale tan oil;

73) 4-{4-[3-(2,4-Difluorophenyl)-l-heptylureidomethyl]phenoxy)butanol-ol, mp 65°-66° C.;

74) 1-(2-Ethoxyphenyl)-3-heptyl-3-[4-(4-methoxybutoxy)benzylurea, colourless oil;

75) 4-{4-[3-(2,4-Dimethoxyphenyl)-l-heptylureidomethyl]phenoxy}butanol-oic acid, pale tan oil;

76) 1-[2,4-Dichloro-6-(4-pivaloylbenzyloxy)phenyl]-3-heptyl-3-[4-(2-methoxyethoxymethoxybenzyl]urea, oil;

77) 1-(2-Fluoro-6-[4-(1,1,3,3-tetramethylbutyl)-phenoxy]phenyl)-3-heptyl-3-{4-(2-methoxyethoxymethoxy)benzyl]urea, colourless oil; and 78) 1-[2,4-Dimethoxy-6-(a-neopentylbenzyloxy)-phenyl]-3-heptyl-3-[4(2-methoxyethoxymethoxy)benzyl]urea.

PHARMACEUTICAL FORMULATION EXAMPLES

In the following Examples, the "active ingredient" is any compound of formula (I) as hereinbefore defined, preferably one of the compounds of Synthetic Examples 1 to 78.

| Tablet | Per tablet |
| --- | --- |
| Active ingredient | 5.0 mg |
| Lactose | 82.0 mg |
| Starch | 10.0 mg |
| Povidone | 2.0 mg |
| Magnesium Stearate | 1.0 mg |
| | 100.0 mg |

Mix together the active ingredient, lactose and starch. Granulate the powders using a solution of povidone in purified water. Dry the granules, add the magnesium stearate and compress to produce 100mg tablets.

| Controlled release tablet | Per tablet |
|---|---|
| Active ingredient | 500 mg |
| Hydroxypropylmethylcellulos (Methocel K4M Premium) | 112 mg |
| Lactose B.P. | 53 mg |
| Povidone B.F.C. | 28 mg |
| Magnesium Stearate | 7 mg |
| | 700 mg |

The formulation may be prepared by wet granulation of the first three ingredients with the solution of povidone, followed by addition of the magnesium stearate and compression.

| Capsule | Per capsule |
|---|---|
| Active ingredient | 250 mg |
| Lactose B.P. | 143 mg |
| Sodium Starch Glycollate | 25 mg |
| Magnesium Stearate | 2 mg |
| | 420 mg |

Capsules may be prepared by admixing the ingredients of the formulation and filling two-part hard gelatin capsules with the resulting mixture.

| Controlled release capsule | Per capsule |
|---|---|
| Active ingredient | 250 mg |
| Microcrystalline Cellulose | 125 mg |
| Lactose BP | 125 mg |
| Ethyl Cellulose | 13 mg |
| | 513 mg |

The controlled-release capsule formulation may be prepared by extruding a mixture of the first three ingredients, then spheronising and drying the extrudate. The dried pellets are coated with the ethyl cellulose as a controlled-release membrane and filled into two-part hard gelatin capsules.

| Powder capsule for inhalation | Per capsule |
|---|---|
| Active ingredient (0.5-7.0 μm powder) | 4.0 mg |
| Lactose (30-90 μm powder) | 46.0 mg |
| | 50.0 mg |

The powders were mixed until homogeneous and filled into suitably sized hard gelatin capsules (50rag per capsule).

| Injectable solution | |
|---|---|
| Active ingredient | 101 mg |
| Glycerol formal | 3.5 ml |

The active ingredient was dissolved in the glycerol formal by shaking the mixture for 2–3 minutes. The resulting solution was distributed into ampoules under aseptic conditions.

| Oral solution A | |
|---|---|
| Active ingredient | 414 mg |
| Glycerol formal | 7.0 ml |

The active ingredient was dissolved in the glycerol formal by shaking the mixture for 2–3 minutes. The resulting solution was distributed into ampoules under aseptic conditions.

| Oral solution B | |
|---|---|
| Active ingredient | 179 mg |
| Labrafil M1944 CS (Gattefosse) | 7.0 ml |

The active ingredient was dissolved in the Labrafil M1944 CS by stirring the mixture at 40°–45° C. for 5–10 minutes. The resulting solution was distributed into ampoules under aseptic conditions.

| Intramuscular injection formulation | |
|---|---|
| Active ingredient | 0.20 g |
| Benzyl Alcohol | 0.10 g |
| Glycofurol 75 | 1.45 g |
| Water for Injection | q.s. to 3.00 ml |

The active ingredient is dissolved in the glycofurol. The benzyl alcohol is added and dissolved, then water added to 3ml. The solution is filtered through a sterile micropore filter and sealed in sterile 3ml glass vials.

| Inhalation aerosol | |
|---|---|
| Active ingredient (0.5–7.0 μm powder) | 200 mg |
| Sorbitan Trioleate | 100 mg |
| Saccharin Sodium (0.5–7.0 μm powder) | 5 mg |
| Methanol | 2 mg |
| Trichlorofluoromethane | 4.2 g |
| Dichlorodifluoromethane | to 10.0 ml |

The sorbitan trioleate and menthol were dissolved in the trichlorofluoromethane. The saccharin sodium and active ingredient were dispersed in the mixture which was then transferred to a suitable aerosol canister and the dichlorofluoromethane injected through the valve system. This composition provides 2mg of active ingredient in each 100 μl dose.

| Syrup formulation | |
|---|---|
| Active ingredient | 0.25 g |
| Sorbitol Solution | 1.50 g |
| Glycerol | 1.00 g |
| Sodium Benzoate | 0.0050 g |
| Flavour | 0.0125 ml |
| Purified Water | q.s. to 5.0 ml |

The sodium benzoate is dissolved in a portion of the purified water and the sorbitol solution added. The active ingredient is added and dissolved. The resulting solution is mixed with the glycerol and then made up to the required volume with the purified water.

| Suppository formulation | Per suppository |
|---|---|
| Active ingredient (63 μm)* | 250 mg |
| Hard Fat, BP (Witepsol H15 - Dynamit Nobel) | 1770 mg |
| | 2020 mg |

*The active ingredient is used as a powder wherein at least 90% of the particles are of 63 μm diameter or less.

One-fifth of the Witepsol H15 is melted in a steam-jacketed pan at a maximum temperature of 45° C. The active ingredient is added to the molten base with mixing, using a Silverson fitted with a cutting head, until a smooth dispersion is achieved. Maintaining the mixture at 45° C., the remaining Witepsol H15 is added to the suspension which is stirred until homogenous. The entire suspension is then passed through a 250 μm stainless steel screen and, with continuous stirring, allowed to cool to 40° C. At a temperature of 38°-40° C., 2.0 g aliquots of the mixture are filled into suitable plastic moulds and the suppositories allowed to cool to room temperature.

| Pessary formulation | Per Pessary |
|---|---|
| Active ingredient (63 μm) | 250 mg |
| Anhydrous Dextrose | 380 mg |
| Potato Starch | 363 mg |
| Magnesium Stearate | 7 mg |
|  | 1000 mg |

The ingredients are mixed directly and pessaries prepared by compression of the resulting mixture.

BIOLOGICAL ASSAYS (i) In vitro assay for the inhibition of ACAT activity
ACAT activity was determined as described by Ross et al by the incorporation of [$^{14}$C]oleoyl-CoA into cholesterol [$^{14}$C]oleate using hepatic microsomes as the source of both ACAT and cholesterol. Microsomes were prepared from the livers of male CD rats fed a 0.8% cholesterol/0.2% cholic acid diet 3.5 days before sacrifice. Various concentrations of a test compound were preincubated with a 0.5mg/ml microsomal suspension and after 15 minutes a 50 μg aliquot was removed and incubated with 25 μM of [$^{14}$C]-enriched oleoyl-CoA for 4 minutes. The reaction was terminated by the addition of 1 ml of ethanol and 4ml of hexane. After shaking, the hexane layer was removed and evaporated to dryness. The hexane extract was then reconstituted in 150 μl of HPLC solvent and injected on to a B&J OD5 Reverse Phase C18 column using an isocratic mobile phase of acetonitrile: isopropanol:heptane (50:40:10) in 0.5% acetic acid at a flow rate of 1.0ml/min. The product of the reaction, [14C]oleoyl cholesterol, was measured using a Flow One radiometric detector.

The ACAT IC$_{50}$ value for each compound was determined from a plot of % inhibition from control vs inhibitor concentration. The IC$_{50}$ for the compound of Synthetic Example 1 was 27nM.

(ii) Determination of hypolipidaemic activity in cholesterol-cholic acid fed rats
Male Sprague-Dawley rats (CD, Charles River) each weighing 200-300 g were used. Hypercholesterolemia was induced in the rats by administration of a diet enriched to 0.4% cholesterol, 0.2% cholic acid. Prior to the administration of the diet, blood samples were collected under halothane anesthesia by cardiac puncture to determine baseline lipid levels. The blood was allowed to clot and serum was obtained for the analysis of total cholesterol, dextran-precipitable lipoproteins cholesterol (VLDL +LDL) and total triglycerides. The rats were divided into groups so that each group had similar average baseline serum lipid levels. Five days after the initial blood sampling, administration of each test compound and the cholesterol-cholic acid-enriched diet was begun. Compounds to be tested by gavage were administered b.i.d. in 0.5% methyl cellulose at 9:00 a.m. and 3:00 p.m. for three days and at 9:00 a.m. on the fourth day. Compounds administered as part of the diet were dissolved in ethanol and sprayed on to the diet. The ethanol was allowed to evaporate and the diet given to the rats for three days. On the fourth day, blood samples were collected and the final serum lipid levels determined. All blood samplings were taken after a four-hour fast. The compound of Synthetic Example 1 at a dose of 25 mg/kg reduced LDL-cholesterol by 78% and at a dose of 50 mg/kg by 92%.

I claim:
1. A compound of formula I

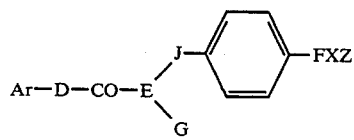

wherein;
Ar is phenyl or naphthyl substituted by one or more atoms or groups independently selected from halogen, C$_{1-8}$ alkyl, C$_{1-8}$ alkoxy (including cycloalkylalkoxy), said alkyl and/or alkoxy group(s) being optionally substituted by one or more halogen atoms. C$_{1-8}$ thioalkyl, aryl, aryloxy and aralkoxy, said aralkoxy group being optionally substituted by alkyl, alkoxy, or hydroxyalkyl:
D is —NH—;
E is —N;
F is —O—;
G is C$_{5-8}$ straight or branched alkyl, (4-halophenyl)C$_{1-3}$ alkyl, or [4-di(C$_{1-6}$ alkyl)aminophenyl]C$_{1-3}$ alkyl:
J is C$_{1-3}$ alkylene:
X is methylene, —CH$_2$CH$_2$—, —CH$_2$OCH$_2$CH$_2$—, —CH$_2$CH(OCH$_3$)—, —CH$_2$CH— (OCH$_2$CH$_3$)—, or —CH$_2$CH$_2$OCH$_2$CH$_2$—; and
Z is C$_{1-4}$ alkoxy;
and physiologically functional derivatives thereof.
2. A compound which is selected from the group consisting of
1-[4-(1,2-dimethoxyethoxy)-benzyl]-3-(2,4-dimethoxyphenyl)-1-heptylurea,
1-heptyl-3-(2,4-dimethoxyphenyl)-1-(2-methoxyethoxymethoxy)-benzyl]urea,
1-(2,4-difluoro-6-methoxyphenyl)-3-heptyl-3-[4-(2-methoxyethoxymethoxy)benzyl]urea,
1-(4-chloro-2-ethoxyphenyl)-3-heptyl-3-[4-(2-methoxyethoxymethoxy)benzyl]urea, and
1-(4-chloro-2-trifluoromethylphenyl)-3-heptyl-3-[4-(2-methoxyethoxymethoxy)benzyl]urea.
3. A method of treating atherosclerosis which comprises the administration of an effective amount of the compound of claim 2 or claim 1.
4. A medicament comprising the compound of claim 2 together with a pharmaceutically acceptable carrier.

* * * * *